United States Patent
Hermanson et al.

(10) Patent No.: US 7,775,069 B1
(45) Date of Patent: Aug. 17, 2010

(54) THERAPEUTIC STOCKING

(75) Inventors: Jon Hermanson, Knoxville, TN (US);
Jim Tipton, Kingston, TN (US); Willie York, Harriman, TN (US)

(73) Assignee: Albahealth, LLC, Rockwood, TN (US)

( * ) Notice: Subject to any disclaimer, the term of this patent is extended or adjusted under 35 U.S.C. 154(b) by 0 days.

(21) Appl. No.: 12/485,117

(22) Filed: Jun. 16, 2009

Related U.S. Application Data

(63) Continuation-in-part of application No. 11/607,607, filed on Dec. 1, 2006, now Pat. No. 7,562,541.

(51) Int. Cl.
*D04B 11/34* (2006.01)
(52) U.S. Cl. .................................................. 66/186
(58) Field of Classification Search ............... 66/178 R, 66/182–187
See application file for complete search history.

(56) References Cited

U.S. PATENT DOCUMENTS

| | | | | |
|---|---|---|---|---|
| 1,811,786 A | * | 6/1931 | Frei .............................. | 66/187 |
| 3,975,929 A | * | 8/1976 | Fregeolle ...................... | 602/63 |
| 4,054,129 A | * | 10/1977 | Byars et al. .................. | 601/152 |
| 4,149,274 A | * | 4/1979 | Garrou et al. ................... | 2/239 |
| 4,150,442 A | * | 4/1979 | Boone .......................... | 602/63 |
| 4,153,050 A | * | 5/1979 | Bishop et al. ................ | 601/152 |
| 4,153,054 A | * | 5/1979 | Boone ........................ | 128/856 |
| 4,341,095 A | | 7/1982 | Poteat .......................... | 66/177 |
| D275,715 S | * | 10/1984 | Boone .......................... | D2/994 |
| 4,557,381 A | * | 12/1985 | Whitney ...................... | 206/440 |
| 4,745,917 A | * | 5/1988 | Hasty et al. ................... | 602/63 |
| 5,103,656 A | * | 4/1992 | Hanson, II .................... | 66/185 |
| 5,724,836 A | * | 3/1998 | Green .......................... | 66/185 |
| 5,814,003 A | * | 9/1998 | Knox et al. .................... | 602/63 |
| 6,012,177 A | * | 1/2000 | Cortinovis ..................... | 2/239 |
| 6,105,173 A | * | 8/2000 | Brown ........................... | 2/239 |
| 6,216,495 B1 | * | 4/2001 | Couzan et al. ................ | 66/183 |
| 6,371,933 B1 | * | 4/2002 | Gardon-Mollard ........... | 602/62 |
| 6,708,348 B1 | * | 3/2004 | Romay ........................ | 2/239 |
| 7,007,517 B2 | * | 3/2006 | Menzies ...................... | 66/185 |

* cited by examiner

*Primary Examiner*—Danny Worrell
(74) *Attorney, Agent, or Firm*—Baker Donelson

(57) ABSTRACT

A therapeutic compression stocking is knitted in an integrated knit format to have an oversized heel pocket from which an ankle arch portion extends that is knitted in a rib stitch format that is free of wrinkles when donned. The foot portion has a constant compression force while the leg portion has a graduated compression force. The leg portion compression force being less than the foot portion compression force.

13 Claims, 3 Drawing Sheets

THERAPEUTIC STOCKING

REFERENCE TO RELATED APPLICATION

This is a continuation-in-part of U.S. patent application Ser. No. 11/607,607 filed Dec. 1, 2006.

TECHNICAL FIELD

This invention relates generally to therapeutic stockings and more specifically to compression stockings that are produced in an integrated knit stitch format.

BACKGROUND OF THE INVENTION

Heretofore compression stockings have been designed to address specialized needs of both athletes and medical patients. Venous disorders provide the most prevalent need today for such stockings. More specifically, they have been designed and developed to apply different degrees of pressure to different portions of the body parts over which they are worn for enhanced venal flow. Exemplary of such compression stockings are those described and shown in U.S. Pat. Nos. 4,745,917, 6,012,177, 6,105,173, 6,216,495 and 6,371,933.

With some compression stockings however excessive stress is produced on the yarns and knit structures in the heels of the stockings while being donned. In other cases wrinkling occurs in the foot crest or arch, also known as the malleolar region, of the stocking over the ankle circumferentially opposite the heel once the stocking has been donned. This wrinkling can cause dermatological irritation which is commonly known as necrosis or skin shearing. These problems have been addressed by providing a stocking gap in the area of the heel. However this, of course, exposes the heel and stresses the gap boundary of the stocking stitching. In other cases one or more patches have been sewn into these problem areas. This approach however negates the stocking from being produced in an integrated knit stitch format with its attendant manufacturing efficiency. It also fails to produce a seamless product.

SUMMARY OF THE INVENTION

In a preferred form of the invention a therapeutic compression stocking for venous disorders which comprises a foot portion having a knit format and yarn to produce a first compression force, an arch portion coupled to the foot portion having a knit format and yarn to produce a second compression force equal to or less than the first compression force, and a leg portion coupled to the arch portion opposite the foot portion having a knit format and yard to produce a third compression force of a graduated compression type. The compression force of the leg portion decreases from a first end adjacent the arch portion to a second end distal the arch portion.

DETAILED DESCRIPTION

Figure 1:
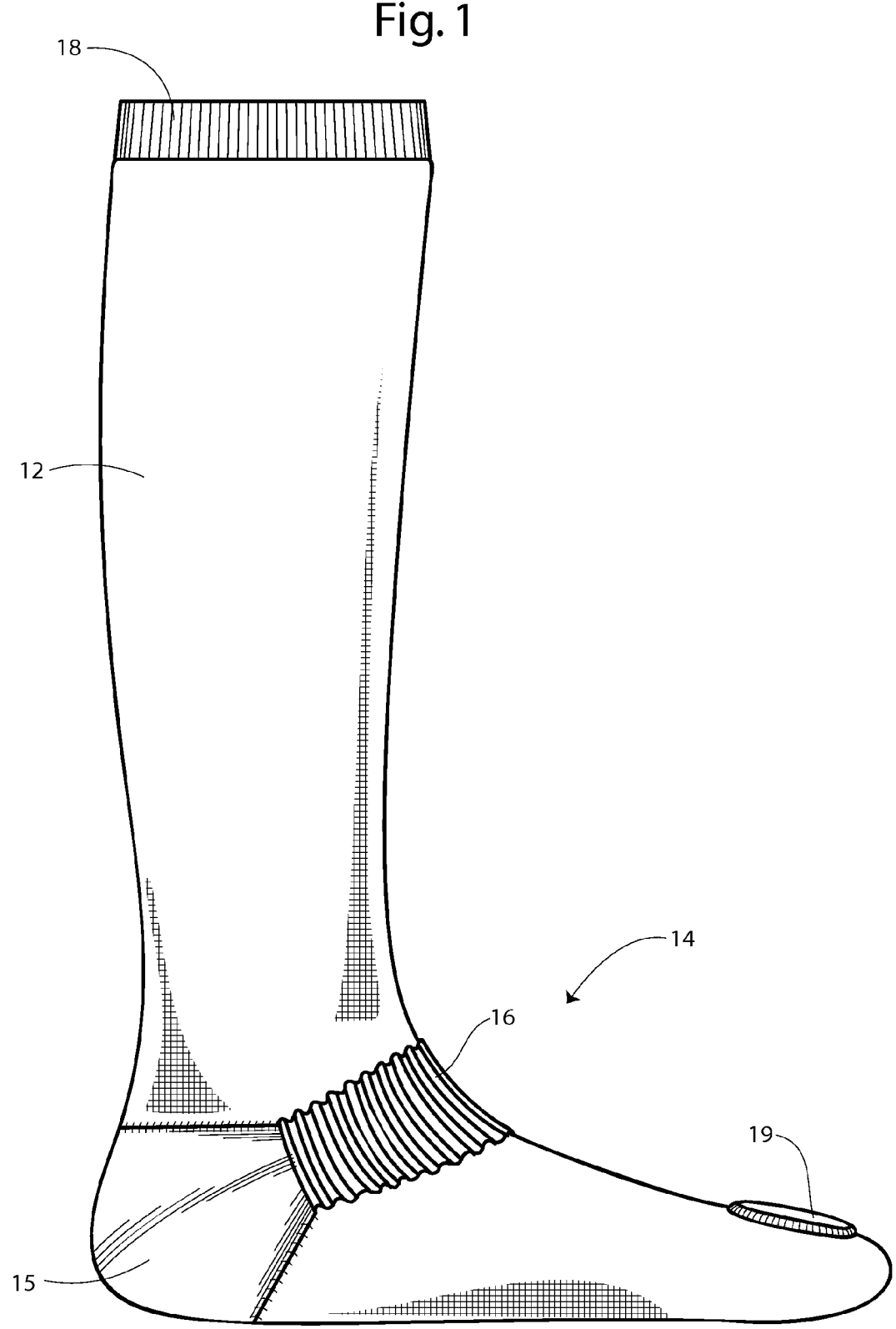
FIG. 1 is a side view of a preferred form of the stocking shown in a worn state, the opposite side being substantially a mirror image thereof.

With reference next to the drawing the seamless therapeutic compression stocking 10 is seen to have a leg portion 12 joined to a foot portion 14 by a heel pocket 15 and an ankle crest or arch portion 16. The leg portion may be of various lengths such as to end below or above the knee at a cuff 18. The top of the foot portion is formed with an opening above the toes bounded by a cuff 19. The stocking may, of course, be produced in any number of overall sizes to fit patients of different sizes.

The stocking is efficiently produced in an integrated knit stitch format with a knitting machine that has needle by needle selection capability in order to produce a stocking without seams. Exemplary of such commercial knitting machines are the Lonati Models 304 and 404. Such a machine can change the stitching needle by needle as the stocking is knitted in tubular from one end to another. The machine thus can be programmed to alter the stitch format from one portion of the stocking to another with yarns extending continuously from one stocking end to the other. Thus the stocking can be made seamless.

With continued reference to the drawing, the leg portion 12 is conventionally knitted in a graduated compression format so that it is tightest when donned at its lower end adjacent the heel pocket 15 and arch portion 16 and gradually becomes less tight higher up the leg. This serves to force blood towards the cardiac cavity of the patient. The foot portion 14 is of a conventional compression knit construction, but is of a constant compression force format along the entire length of the foot portion rather than of a graduated compression force format. The compression force of the leg portion is preferably 40% to 50% of the compression force of the foot portion to prevent a tourniquet effect upon the veins, thereby pinching the veins, which would cause blood to pool within a wearer's foot. The compression force of the leg portion should not exceed 75% of the compression force of the foot portion. Additionally, the compression force of the leg portion is preferably 50% of the compression force of the arch portion 16, while the compression force of the foot portion is approximately that of the arch portion 16. Typically, the arch portion 16 has a compression force of between 18 and 20 mm of water and the leg portion has an end which commences adjacent the arch portion with a compression force of approximately 18 mm of water and terminates at an opposite end adjacent the cuff, or distal the arch portion, with a compression force of approximately 8 to 10 mm of water.

The heel pocket 15 here is knitted so as to be oversized relative to the foot and leg portions. This is done by programming the machine to loosen and open up each knitted loop of the stitching. Conversely, an oversized heel has traditionally been formed as a patch with similar relaxed and cross stretch properties as the balance of the stocking in the area adjacent to the heel. This, of course, requires patching to be introduced into the overall manufacturing process which impedes efficiency of production and introduces seams.

By the heel being oversized relative to other portions of the stocking, when the stocking is laid out as a flat tubular blank, the heel is slightly wrinkled. The stitch loops of the oversized heel pocket are knitted looser than the stitch loops of the leg and foot portions so as to have some one-third or more elongation than these other portions. As such, the heel portion has a compression force that is less than the compression force of the leg portion. This serves to facilitate donning where the outcropped heel provides a donning impediment. This is especially beneficial where a wound dressing has been applied to the patient's heel. This construction also insures that minimal tension is placed on the yarns of the heel pocket while the stocking is being donned. The compression force of the heel pocket may be less than that of the leg portion without causing blood pooling because the heel portion has few veins, i.e., the heel has very limited vessel population compared to surrounding tissues. The oversized heel forms a less restrictive pocket for the foot to fit. Without this aspect, the fabric is stretched vertically around the heel, which could compromise the horizontal compression at the ankle.

Figure 2:
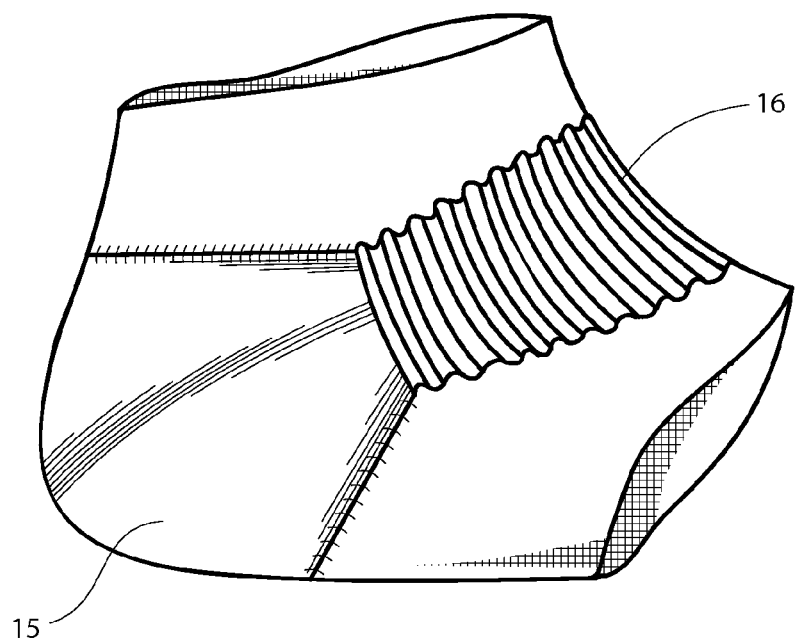
FIG. 2 is an enlarged view of a portion of the stocking shown in FIG. 1.
Figure 3:
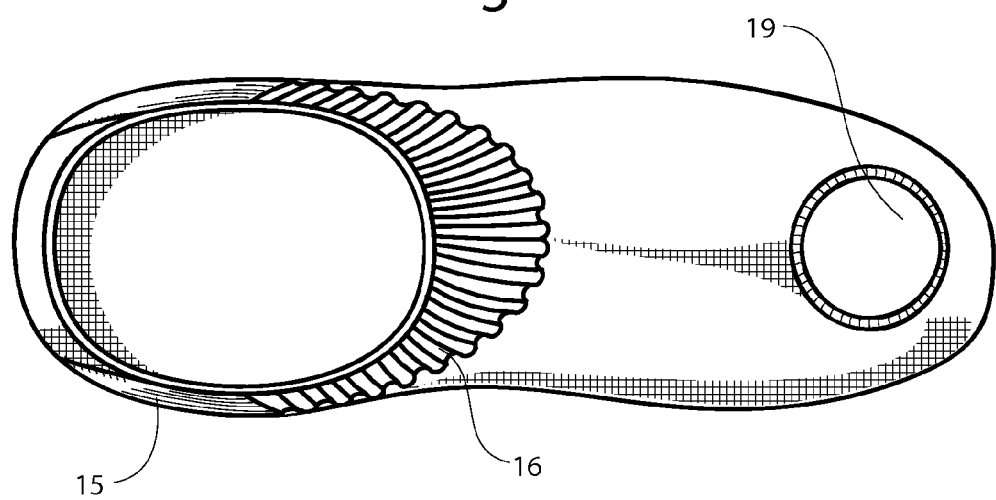
FIG. 3 is a top view of the stocking shown in FIG. 1.

The ankle crest or arch portion 16 is knitted in a manner that substantially prevents it from wrinkling when donned as would occur if it were of the same stitch format as that of the heel pocket, leg or foot portion. This is achieved by programming the knitting machine to gather the excess stitches here into a multi-ribbed format, wherein the ribs extend longitudinally up the leg between the foot portion and leg portion, as shown most clearly in FIG. 2. Once donned the gathered ribs become ungathered and smooth without wrinkles. Otherwise, were wrinkles to remain here the skin beneath this arch would become subject to abrasion.

Figure 4A:
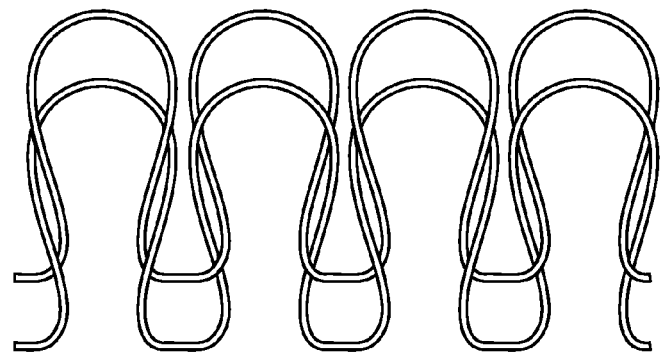
FIGS. 4A-4C illustrated 1×1, 2×2 and 3×1 knit rib formats, respectively.
Figure 4B:
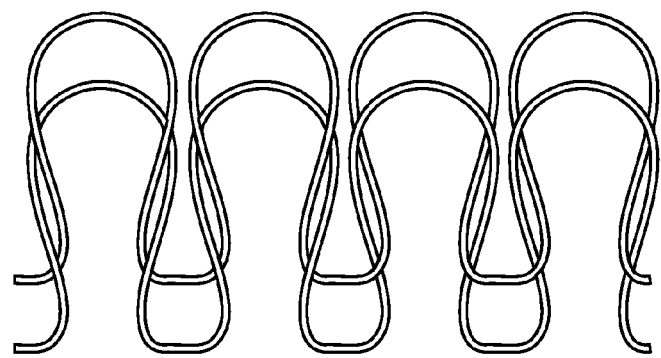
Figure 4C:
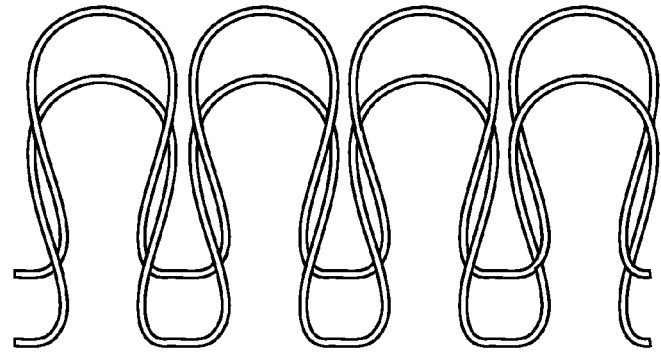

The ankle arch portion is preferably knitted in a 1×1, a 2×2 or a 3×1 rib format, depending on the thermo-plastic properties, modulus and size of the yarns. These formats are illustrated in FIGS. 4A-4C. In FIG. 4A it is seen that alternating wales are looped to the front and then to the back. As viewed here from left to right, the upper loop is over the top of the lower. The next loop is under, the next over, the next under, and so forth. This is a 1×1 format. In FIG. 4B every two adjacent wales are looped over and the next two under, again as viewed from left to right. This is a 2×2 format. FIG. 4C shows a 3×1 rib format or structure where three wales are looped over and then one wale is looped under, and so forth. Preferably the ankle arch portion is knitted directly to the heel pocket although this is not essential.

The preferred stocking yarns here are stretch nylon and spandex, spandex being an elastic fiber sold under the trade name LYCRA and available from E. I. DuPont de Nemours and Company, Wilmington, Del., U.S.A. Stretch nylon and spandex are synthetic fibers that are resilient. The degree of stretch and recovery of these fibers can be thermally altered to a desired modulus.

Preferably the foot cuff 18 and heel border are color coded for ease in orienting the stocking for donning. This contrasting color can be provided topically or by differentiating yarn color selection. The term wrinkle is intended to mean unintended bends or crimps in yarn, mis-shaped stitches, or excess material that adversely affects the presentation, hand, or performance of a fabric or the end product.

It thus is seen that a therapeutic compression stocking may now be manufactured in an integrated knit stitch format that my be donned with facility over the heel and which provides improved graduated pressure between the heel and the leg and foot portions all without wrinkling of the stocking over the ankle arch. Although the stocking has been illustrated and described in its preferred form, it should be understood that many modifications, additions and deletions may be made to that specific form without departure from the spirit and scope of the invention as set forth in the following claims.

The invention claimed is:

1. A therapeutic compression stocking for venous disorders comprising a foot portion having a knit format and yarn to produce a first compression force, an arch portion coupled to said foot portion having a knit format and yarn to produce a second compression force equal to or less than said first compression force, said arch portion extending longitudinally and laterally so as to have a desired surface area to cover a majority of the surface area of a wearer's foot top arch, and a leg portion coupled to said arch portion opposite said foot portion having a knit format and yarn to produce a third compression force of a graduated compression type wherein the compression force decreases along the leg portion from a first end adjacent said arch portion to a second end distal said arch portion.

2. The therapeutic compression stocking of claim 1 wherein said foot portion second compression force is generally constant along the entire length of said foot portion.

3. The therapeutic compression stocking of claim 1 further comprising a heel portion coupled to and between said foot portion and said leg portion and adjacent said arch portion, said heel portion having a fourth compression force less than said leg portion third compression force.

4. The therapeutic compression stocking of claim 1 wherein said ankle arch portion knit format is in a pattern of ribs that extend side by side in a longitudinal direction between the leg and foot portions.

5. The therapeutic compression stocking of claim 1 wherein said ankle arch portion is knitted in a 1×1 or a 2×2 or a 3×1 knit stitch format.

6. The therapeutic compression stocking of claim 1 wherein said foot portion, said arch portion and said leg portion are constructed of an integrated knit stitch format which produces no seams between adjacent portions.

7. A therapeutic compression stocking having tubular knitted yarn foot and leg portions joined by a knitted yarn foot arch portion, said arch portion extending longitudinally and laterally so as to have a desired surface area to cover a majority of the surface area of a wearer's foot top arch, wherein said foot portion is knitted with a constant compression format, wherein said leg portion is knitted with a graduated knit format that decreases the compression force of the stocking leg portion from a first end adjacent said arch portion to a second end distal said arch portion.

8. The therapeutic compression stocking of claim 7 wherein said foot portion constant compression format has a first compression force and said leg portion graduated knit format has a second compression force less than said first compression force.

9. The therapeutic compression stocking of claim 7 wherein said arch portion has a third compression force, and wherein said arch portion third compression force is greater than said leg portion second compression force.

10. The therapeutic compression stocking of claim 9 further comprising a heel portion coupled to and between said foot portion and said leg portion and adjacent said arch portion, said heel portion having a fourth compression force less than said leg portion second compression force.

11. The therapeutic compression stocking of claim 7 wherein said ankle arch portion knit format is in a pattern of ribs that extend side by side in a longitudinal direction between the leg and foot portions.

12. The therapeutic compression stocking of claim 7 wherein said ankle arch portion is knitted in a 1×1 or a 2×2 or a 3×1 knit stitch format.

13. The therapeutic compression stocking of claim 7 wherein said foot portion, said arch portion and said leg portion are constructed of an integrated knit stitch format which produces no seams between adjacent portions.

* * * * *